United States Patent [19]

Debras et al.

[11] Patent Number: 4,556,753
[45] Date of Patent: Dec. 3, 1985

[54] PROCESS FOR PRODUCING ISOBUTENE

[75] Inventors: Guy L. G. Debras, Belgrade; Georges E. M. J. De Clippeleir, Sint Pieters; Raymond M. Cahen, Brussels, all of Belgium

[73] Assignee: Labofina, S.A., Brussels, Belgium

[21] Appl. No.: 719,192

[22] Filed: Apr. 3, 1985

[30] Foreign Application Priority Data

Apr. 3, 1984 [LU] Luxembourg ............................. 85284

[51] Int. Cl.$^4$ ................................................ C07C 6/00
[52] U.S. Cl. ..................................................... 585/643
[58] Field of Search ......................................... 585/643

[56] References Cited

PUBLICATIONS

Banks et al., *Ind. Eng. Chem. Prod. Res. Develop.*, vol. 10, No. 1, (1971), pp. 46–51.

*Primary Examiner*—Curtis R. Davis
*Attorney, Agent, or Firm*—John K. Abokhair; M. Norwood Cheairs

[57] ABSTRACT

A process for producing isobutene, comprising contacting, at elevated temperatures, a feed containing propylene with a catalyst comprising a crystalline silica polymorph of the silicalite type in the presence of steam to recover a stream containing isobutene. The reaction can be carried out in either liquid or vapor phase.

10 Claims, No Drawings

PROCESS FOR PRODUCING ISOBUTENE

FIELD OF THE INVENTION

The present invention relates to a process for selectively producing isobutene from propylene or from a mixture of hydrocarbons containing propylene.

BACKGROUND OF THE INVENTION

The environmental and other governmental measures adopted by several countries against the use of tetraethyllead in motor-fuel led the petroleum industry to seek other additives, including oxygen-containing additives, for improving the octane number of motor-fuel. Among these additives, asymmetric ethers, and more particularly methyl tert-butyl ether (MTBE), have proved to be very efficient gasoline additives. The most common method for the preparation of MTBE comprises the reaction of isobutene with methanol.

Isobutene is also used as starting material for the production of other valuable compounds, such as t-butyl alcohol (used as solvent), t-butyl phenol (used as stabilizer), low molecular weight polymers (used to improve the viscosity index of lubricating oils), etc. As a result of this increased interest in isobutenes, the present availability of isobutene does not allow the production of sufficient amounts of these derivatives to satisfy their potential market.

Accordingly, it can be seen that presently there is a need for a process to simply and economically produce isobutene, and particularly, a process that can utilize starting materials which are readily available.

One of the continuing problems in a petroleum refinery when using catalytic cracking processes is handling the very large amounts of gas produced. Catalytic cracking, and especially fluid catalytic cracking (FCC), is widely used in petroleum refineries. Refiners have more capacity for catalytic cracking than for any other single process except distillation. Since catalytic cracking is a non-hydrogenative process, it can be appreciated that huge amounts of olefinic gases are produced. Whenever the severity of a catalytic cracker is increased or the throughput is increased, even more olefinic gases are produced.

Recovering these enormous amounts of gas for further reaction requires large capital outlays for compressors and gas handling equipment. The alternative is to burn the olefinic gases as fuel for other parts of the refinery or as waste. Unfortunately, because the quantities of gas are huge and the capital costs are high, these gases are too often burned instead of recovered and reacted. $C_3$ and lower gases comprise the majority of wasted gases.

It can be appreciated that there is a highly intensive search for efficient, economical processes which would allow these reactive olefinic gases to be used further as chemicals rather than to be wasted. These olefinic gases often contain propylene, which is of particular interest in the present invention.

Several processes for upgrading these olefinic gases have been described in the literature. U.S. Pat. No. 4,414,423 to S. J. Miller discloses a method for upgrading feeds containing normally gaseous olefins by an oligomerisation reaction in at least two steps leading to the formation of high boiling point hydrocarbons. This method may be applied to propylene or to a mixture of propane and propylene as starting materials. Normally, liquid olefins are formed by oligomerisation in a first step, and are subsequently converted into higher oligomers in a second step. The object of the method described in this patent is to give good yields of high boiling point hydrocarbons. During the first step, a minimal amount of $C_4$ olefins (of which isobutene is only one of the three isomers), is formed starting from a mixture of propane and propylene. Therefore, such a method cannot be used for the selective production of isobutene from propylene or from a gaseous feed which contains propylene. U.S. Pat. No. 4,417,086 to Miller and U.S. Pat. No. 4,417,088 to Miller disclose processes for oligomerizing liquid olefins using intermediate pore size molecular sieves. However, none of these presently known processes can be utilized for the production of significant amounts if isobutene.

SUMMARY OF THE INVENTION

An object of the present invention is to provide a new process for producing isobutene.

Another object of the present invention is to provide an economical process for selectively transforming propylene into isobutene.

Still another object of the invention is to selectively produce isobutene from propylene or from a propylene-containing feed.

The process of the present invention essentially comprises contacting a propylene-containing feed with a catalyst consisting of crystalline silica polymorph of the silicalite type, in the presence of steam, the molar ratio of water/feed being from about 0.5 to about 5.

DETAILED DESCRIPTION OF THE INVENTION

As starting feed for the process of the present invention, essentially pure propylene or fractions obtained during the refining process and which may contain as little as 10 vol. % of propylene may be used. Said fractions may contain other low molecular weight olefinic hydrocarbons, as well as saturated hydrocarbons having from 1 to 4 carbon atoms, including propane which is also partially converted by the process of the present invention.

The catalyst utilized in the present invention is an unmodified crystalline silica polymorph of the silicalite type. Therefore, the catalyst is a substantially pure silica, which means that it does not contain either impurities or modifying elements or that it only contains traces of them. The preparation method and the structure of such silicalite type catalysts are described in U.S. Pat. No. 4,061,724 by Grose, which is hereby incorporated by reference in its entirety.

The propylene-containing feed is contacted with silicalite in the presence of steam. It has indeed been unexpectedly found that the presence of water results not only in improving the lifetime of the catalyst, but also, and more importantly, in promoting the production of butenes, and in particular of isobutene, by reducing the formation of heavier products. Due to the presence of steam, the isobutenes selectivity is increased by about 50%, all other factors being equal. The term "isobutene selectivity" means the weight of isobutene formed, calculated on 100 parts by weight of converted feed. This improvement in selectivity is achieved even when the feed is treated in the presence of an amount of water of the order of as little as 0.5 mole of water per mole of feed. Comparative trials have also shown that it is preferable to maintain a molar ratio of water/feed which does not exceed about 5. This upper limit varies according to several factors including the composition of the feed. For example, the molar ratio of water/feed is preferably lower than about 1.5 when the feed is formed of a mixture of propane and propylene containing about 10% by weight of propylene. Preferably, the amount of water used is such that the molar ratio of water/feed is from about 0.5 to about 1, however, the ratio may be higher when the feed has a high propylene content.

The method of the present invention is very flexible and may be applied in the gaseous and/or in the liquid phase. Reaction temperatures are generally from about 300° to about 550° C. Temperatures lower than 300° C. give very low yields, while temperatures higher than 550° C. cause some degradation of the reaction products. Generally, temperatures of from about 300° to about 500° C. and more particularly, from about 320° to about 475° C. are preferred. Temperature variations within these limits do not significantly modify the distribution of the products formed.

The hourly space velocity of the reaction mixture, expressed by the weight amount of said mixture by hour and by weight of catalyst (WHSV), may vary from about 5 to about 100. The WHSV depends on among other factors, the composition of the feed. A high space velocity allows for a better isobutene selectivity but to the detriment of the conversion rate of the feed. Whenever the feed consists essentially of propylene, the WHSV used is preferably from about 75 to about 125, whereas when the feed contains about 10% propylene, the WHSV is preferably from about 25 to about 80.

The pressure at which the reaction is carried out may vary within a rather wide range, e.g., between subatmospheric pressure and an absolute pressure of 50 bars. A typical range of absolute pressure to carry out the reaction is from about 0.5 to about 20 bars. It is advantageous to work at low pressures to favor the production of isobutene.

One skilled in the art can determine within the abovementioned ranges, the operating conditions which will give the best yields considering not only the composition of the feed but also the desired results. Thus, certain conditions, like a high WHSV, favor the formation of isobutene with a low conversion rate of the feed; under such conditions, it is advantageous to recover the isobutene from the reaction products, then to recycle the isobutene-free reaction products to submit them to a new treatment along with fresh feed.

The following examples are meant to be illustrative and are not intended to describe the limits of the present invention.

EXAMPLE 1

Propylene and steam were passed together over silicalite at 397° C., under a pressure of 1 bar, with a molar ratio water/feed of 0.75 and a WHSV of 93.2.

51.1% of the propylene was converted, and the selectivity for isobutylene was 18.68%.

EXAMPLE 2

Propylene and steam were passed together over silicalite at 309° C., under a pressure of 0.8 bar, with a molar ratio water/feed of 0.72 and a WHSV of 97.2.

The reaction products had the following composition:

| | | |
|---|---|---|
| $C_1$–$C_2$ | 1.4% | by weight |
| non-converted propylene | 36.3 | |
| propane | 1.0 | |
| all butenes | 29.6 | (including isobutene) |
| $C_5$ | 30.5 | |

The isobutene selectivity was 19.19 weight %.

EXAMPLE 3

A feed, containing 71.07 wt % of propylene and 28.93 wt % of propane, was passed together with steam over silicalite at a temperature of 350° C., under a pressure of 14 bars, with a molar ratio of water/feed of 0.92 and a WHSV of 76.6.

The conversion rate of propane was 11.3 wt % and that of propylene 81.7 wt %. The isobutene selectivity was 12.63¢.

EXAMPLE 4

A feed, containing 89.31 wt % of propane and 10.69 wt % of propylene, was passed together with steam over silicalite at a temperature of 349° C., under a pressure of 15 bars, with a molar ratio of water/feed of 0.88 and a WHSV of 73.2.

8.3% by weight of the propane and 70.7% by weight of the propylene were converted. The isobutene selectivity was 14.46%.

EXAMPLE 5

Propylene was passed together with steam over silicalite at a temperature of 301° C., under atmospheric pressure, with a molar ratio of water/feed of 0.82 and a WHSV of 5.2.

The conversion rate of propylene was 93.8% and the isobutene selectivity was 10.27%.

For comparative purposes, the same experiment was repeated, however, in the absence of steam.

The isobutene selectivity was of only 6.93%.

EXAMPLE 6

A feed, containing 71 wt % of propylene and 29 wt % of propane, was passed together with steam over silicalite at a temperature of 400° C., under a pressure of 14.7 bars, with a molar ratio of water/feed of 2.62 and a WHSV of 32.8.

13.4 wt % of the propane and 80.1 wt % of the propylene were converted, and the isobutene selectivity was 13.14%.

EXAMPLE 7

Propylene was passed together with steam over silicalite at a temperature of 301° C., under atmospheric pressure, with a molar ratio of water/feed of 1.64 and a WHSV of 5.26.

90.4 wt % of the propylene was converted and the isobutene selectivity was of 10.95%.

For comparative purposes, the same feed was passed, without water vapor, over silicalite at a temperature of 300° C., under atmospheric pressure and at a WHSV of 5.24. The isobutene selectivity was of only 5.91% and the conversion rate of propylene was of 95.0%.

EXAMPLE 8

Propylene was passed together with steam over silicalite at a temperature of 310° C., under a pressure of 0.8 bar, with a molar ratio of water/feed of 0.72 and a WHSV of 97.1.

After 10 hours, the conversion rate of the propylene was 63.7% and the isobutene selectivity was of 19.19%.

For comparative purposes, the same propylene feed was passed, in the absence of steam, over silicalite at a temperature of 310° C., under a pressure of 0.8 bar and at a WHSV of 95.8. After 10 hours, the conversion rate of the propylene was 58.2% and the isobutene selectivity was only 4.1%.

As can be seen from the above, the process of the present invention results in the production of substantially above stoichiometric amounts of isobutene. For example, in Example 8, the presence of steam increased the isobutene selectivity by more than 400%.

Although the present invention has been described with preferred embodiments, it is to be understood that modifications and variations may be resorted to, without departing from the spirit and scope of this invention, as those skilled in the art will readily understand. Such modifications and variations are considered to be within the purview and scope of the appended claims.

What we claim is:

1. A process for producing isobutene wherein said process comprises the steps of:
   (a) contacting at a temperature of about 300° C. or higher, a feed containing propylene with a catalyst consisting essentially of a crystalline silica polymorph of the silicalite type in the presence of a sufficient amount of steam such that the water/feed molar ratio is from about 0.5 to about 5; and
   (b) recovering a stream containing isobutene.

2. The process of claim 1, wherein the water/feed molar ratio is from about 0.5 to about 1.

3. The process of claim 1, wherein step (a) is carried out at a temperature of from about 300° C. to about 550° C.

4. The process of claim 1, wherein step (a) is carried out at a temperature of from about 320° C. to about 475° C.

5. The process of claim 1, wherein step (a) is carried out at a weight of reaction mixture per hour and weight of catalyst (WHSV) of from about 5 to about 150.

6. The process of claim 1, wherein step (a) is carried out at a weight of reaction mixture per hour and weight of catalyst (WHSV) of from about 25 to about 125.

7. The process of claim 1 wherein step (a) is carried out at an absolute pressure of from about subatmospheric to about 50 bars.

8. The process of claim 1 wherein step (a) is carried out at an absolute pressure of from about 0.5 to about 20 bars.

9. A process for producing isobutene wherein said process comprises the steps of:
   (a) contacting, at a temperature of from about 320° C. to about 475° C. and under an absolute pressure of from about 0.5 bars to about 20 bars, a feed containing propylene with a catalyst consisting essentially of a crystalline silica polymorph of the silicalite type in the presence of a sufficient amount of steam such that the water/feed molar ratio is from about 0.5 to about 1.5; and
   (b) recovering a stream containing isobutene.

10. A process for producing isobutene wherein said process comprises the steps of:
    (a) contacting, at a temperature of from about 300° C. to about 550° C. and under an absolute pressure of from about 0.5 bars to about 50 bars, a feed containing propylene with a catalyst consisting essentially of a crystalline silica polymorph of the silicalite type in the presence of a sufficient amount of stream such that the water/feed molar ratio is from about 0.5 to about 5; and
    (b) recovering a stream containing isobutene.

* * * * *

UNITED STATES PATENT AND TRADEMARK OFFICE
CERTIFICATE OF CORRECTION

PATENT NO. : 4,556,753
DATED : December 3, 1985
INVENTOR(S) : Guy L.G. Debras, Georges E.M.J. De Clippeleir and Raymond M. Cahen It is certified that error appears in the above—identified patent and that said Letters Patent is hereby corrected as shown below:

In Column 4, line 19, "12.63¢" should read "12.63%".

Signed and Sealed this

Twentieth Day of May 1986

[SEAL]

Attest:

DONALD J. QUIGG

Attesting Officer

Commissioner of Patents and Trademarks